United States Patent [19]

Gostine

[11] Patent Number: 5,544,377
[45] Date of Patent: Aug. 13, 1996

[54] THERAPEUTIC PILLOW FOR LOW BACK PAIN

[76] Inventor: Mark L. Gostine, 3110 Bonnell, S.E., Grand Rapids, Mich. 49506-3136

[21] Appl. No.: 436,566

[22] Filed: May 8, 1995

[51] Int. Cl.⁶ .............................. A47C 20/00; A61G 7/06
[52] U.S. Cl. ..................... 5/630; 5/652; 601/1; 128/845
[58] Field of Search ............................ 5/630, 631, 632, 5/648, 652; 601/1; 606/240; 126/845

[56] References Cited

U.S. PATENT DOCUMENTS

| | | |
|---|---|---|
| D. 250,835 | 1/1979 | Grube . |
| D. 282,036 | 1/1986 | Ritchie, Jr. et al. . |
| D. 282,802 | 3/1986 | Righini . |
| D. 282,803 | 3/1986 | Righini . |
| D. 292,460 | 10/1987 | Malin . |
| D. 306,245 | 2/1990 | Akhtarekhavari . |
| D. 308,455 | 6/1990 | Jenney . |
| D. 322,312 | 12/1991 | Mombrinie . |
| 744,713 | 11/1903 | Blomqvist . |
| 1,398,150 | 11/1921 | Pollard . |
| 1,934,918 | 11/1933 | Everson . |
| 2,336,707 | 12/1943 | Thompson . |
| 2,562,725 | 7/1951 | Leto et al. . |
| 2,612,158 | 9/1952 | Manley ................................ 5/630 X |
| 2,777,440 | 1/1957 | Baker . |
| 2,854,971 | 10/1958 | Williams . |
| 2,952,856 | 9/1960 | Ruff . |
| 3,111,944 | 11/1963 | Puckett ................................ 606/240 |
| 3,234,623 | 2/1966 | Rector . |
| 3,287,747 | 11/1966 | Ellsworth . |
| 3,359,577 | 12/1967 | Rogers ..................................... 5/630 |
| 3,604,023 | 9/1971 | Lynch . |
| 3,811,140 | 5/1974 | Burpo . |
| 3,924,282 | 12/1975 | Bond . |
| 4,288,879 | 9/1981 | Pate . |
| 4,350,152 | 9/1982 | Strakowski .............................. 5/630 X |
| 4,397,052 | 8/1983 | Lund, III . |
| 4,506,396 | 3/1985 | Ritchie, Jr. et al. . |
| 4,923,187 | 5/1990 | Mombrinie . |
| 4,989,591 | 2/1991 | Anders, Jr. . |
| 5,131,410 | 7/1992 | Neill et al. . |
| 5,182,828 | 2/1993 | Alivizatos . |
| 5,216,772 | 6/1993 | Clute . |
| 5,272,780 | 12/1993 | Clute . |
| 5,347,669 | 9/1994 | Neviaser et al. . |
| 5,367,730 | 11/1994 | Sher . |

FOREIGN PATENT DOCUMENTS

| | | |
|---|---|---|
| 154609A1 | 9/1985 | European Pat. Off. . |
| WO91/16842 | 11/1991 | WIPO . |

Primary Examiner—Michael F. Trettel
Attorney, Agent, or Firm—Van Dyke, Gardner, Linn & Burkhart, LLP

[57] ABSTRACT

A therapeutic pillow for relieving various types of low back pain. The pillow comprises two hemispherical end sections joined by an elongated midsection. The midsection is a substantially flat lumbar support portion with sloping surfaces extending to each end section, to provide a pillow that is substantially concave in shape. In use, when sleeping on one's side, the pillow is placed generally transverse to the length of the body under the side. The midsection provides support and alignment for the lumbar spine, thereby relieving pain associated with sagging of the spine. Further, by placing one hemisphere close to the back or hip, the pillow will wrap around the hip area and place pressure on the sacro-iliac joint, for pain relief in that particular area of the body. The pillow can also be placed transverse to the body under the stomach when one sleeps on his or her stomach, again to support and align the lumbar spine. The hemispherical end pads also serve to confine the sleeping person on the pillow and keep the person from rolling out of the pillow.

26 Claims, 3 Drawing Sheets

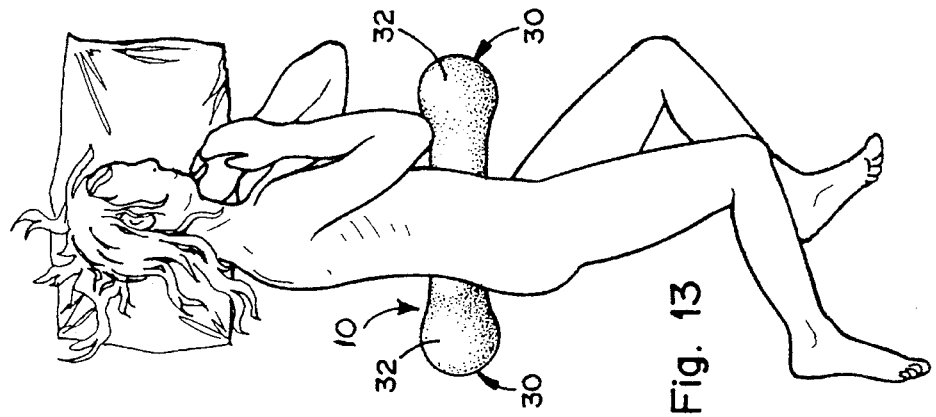

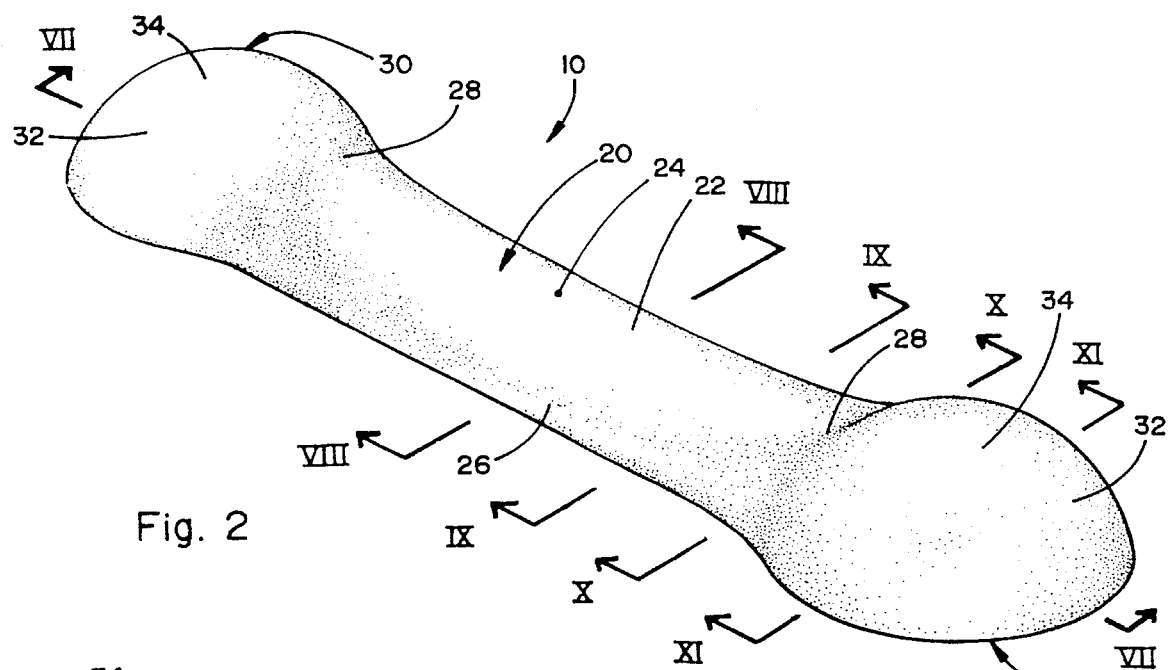
Fig. 2
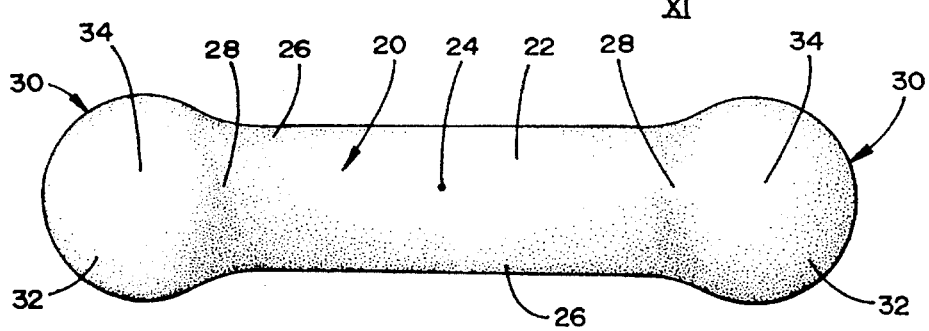
Fig. 3
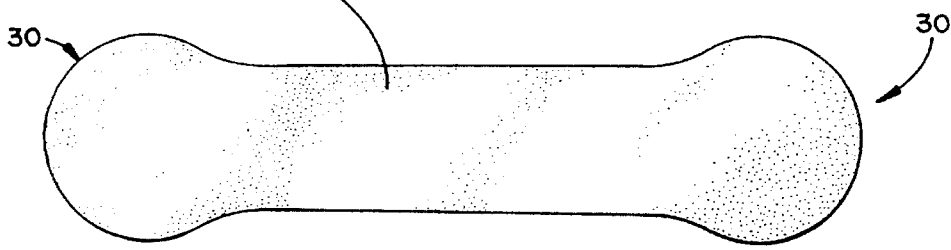
Fig. 4
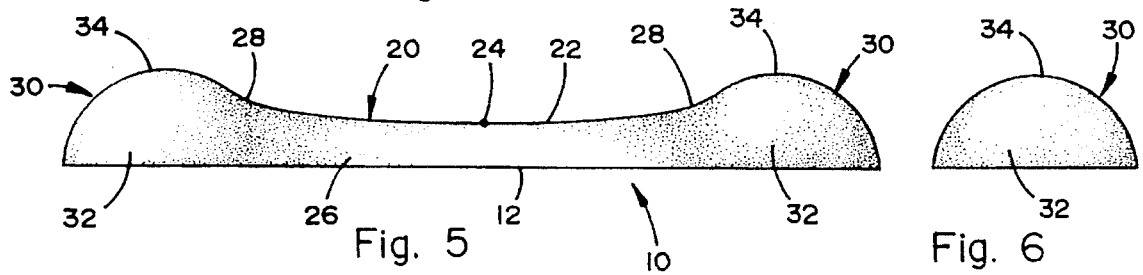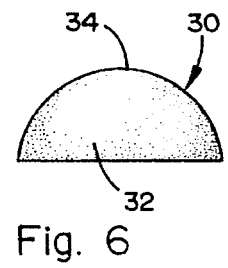
Fig. 5  Fig. 6

5,544,377

THERAPEUTIC PILLOW FOR LOW BACK PAIN

BACKGROUND OF THE INVENTION

The present invention relates to a therapeutic pillow, and particularly to a pillow which prevents and relieves pain associated with the sacro-iliac joint as well as the lumbar spine area.

Numerous attempts have been made to provide a pad or cushion-like structure for engaging or supporting a person's lower back to alleviate pain. Such devices have traditionally been placed under a person's midsection when sleeping on one's stomach, or near the lower spine area when sleeping on one's back. For example, U.S. Pat. No. 4,989,591 to Anders Jr. discloses an orthopedic appliance and method for changing the angular relationship of an individual's longitudinal axis of the lower lumbar spine to the longitudinal axis of the femorae. The device has an upper surface having first and second portions which are angularly disposed to one another to support the hips in the described angular relationship when the person is lying prone over the device. While this device does serve to elevate the lower spine, the device can be the source of other pain or discomfort, due to the shape of the device, which is substantially arc-shaped in cross-section. This type of device tends to be uncomfortable or even painful due to the apparatus gathering or bunching up, and causing the application of localized pressure at the peak of the arc. Furthermore this device is not capable of applying gentle pressure to the back at the hip bone/pelvis region to alleviate pain associated with the sacro-iliac joint. Nor are any of the known devices designed to support and align the spine when a person is lying on his or her side, as opposed to the stomach or back.

Various other devices have been proposed which serve as anti-roll devices during sleep, i.e., to confine or support an adult or infant while sleeping. These devices generally consist of spaced pads or cushions connected by a sheet or connecting member. The pads and connectors take various forms, including triangular, rounded, partially conical, cylindrical, wedge-like, and even slings. See, for example: U.S. Pat. No. 5,367,730 to Sher; U.S. Pat. No. 5,347,669 to Neviaser; U.S. Pat. No. 5,216,772 to Clute; U.S. Pat. No. 5,182,828 to Alivizatos; U.S. Pat. No. 4,923,187 to Mombrinie; U.S. Pat. No. 3,924,282 to Bond; and U.S. Pat. No. 2,952,856 to Ruff. These devices generally make no provision for support of the lower spine. Also, the spaced pads serve no therapeutic function—they merely restrain the person from rolling out of the device.

Therefore, a need exists for a pillow which is not only comfortable, but which also is capable of supporting one's spine when a person is lying on the stomach or when lying on the side. In addition to performing these aforementioned functions, a need also exists for a pillow which is designed to apply pressure to the sacro-iliac joint and thereby reduce or eliminate pain associated with that region of the lower back.

SUMMARY OF THE INVENTION

In the present invention, a pillow is provided for alleviating back pain, and particularly for not only aligning the lower spinal cord area, but also for applying therapeutic pressure to the sacro-iliac joint. The pillow is preferably formed in one piece from flexible, resilient foam material and comprises two hemispherical end sections connected by a midsection. The midsection consists of a substantially flat lumbar support portion with rounded sides. Sloping surfaces connect the end sections to the midsection to provide a pillow that is substantially concave or saddle-like between each hemisphere. The generally flat shape of the lumbar support portion serves to comfortably support the spine when placed transverse to the length of the body under one side or the stomach when sleeping. By placing one end section close to the back or hip when sleeping on one's side, the pillow will wrap around the hip area and cause the apex of the hemisphere to apply pressure to the sacro-iliac joint, thereby relieving pain in that region. The hemispherical end sections also serve to confine and prevent the person from rolling out of the pillow while sleeping.

These and other features, advantages and objects of the present invention will be further understood and appreciated by those skilled in the art by reference to the following specification, claims and appended drawings.

BRIEF DESCRIPTION OF THE DRAWINGS

FIG. 1 is a perspective view of a pillow in accordance with the present invention, shown in position to apply pressure to the sacro-iliac joint of a person lying on one side;

FIG. 2 is a perspective view of the pillow of FIG. 1;

FIG. 3 is a top view of the pillow;

FIG. 4 is a bottom view of the pillow;

FIG. 5 is a side view of one side of the pillow, the opposite side being a mirror image thereof;

FIG. 6 is an end view of one end of the pillow, the opposite end being a mirror image thereof;

FIG. 13 is a top perspective view of a person lying on one side, across the midpoint of the pillow; and FIG. 14 is a perspective view of a person lying on the stomach, across the midpoint of the pillow.

DETAILED DESCRIPTION OF THE PREFERRED EMBODIMENT

In the preferred embodiment, a therapeutic pillow is provided, shown generally in FIGS. 1–11 and 13–14 and depicted by the numeral 10. Pillow 10 is designed to place pressure on the sacro-iliac joint when a person is sleeping on a side with pillow 10 placed transverse to the length of the body and one end of pillow 10 close to the back or the hip. In this position, pillow 10 tends to wrap around the hip area and place pressure on the sacro-iliac joint, thereby relieving pain in this area. Pillow 10 is also designed to support the spine in alignment and prevent it from sagging when placed under one side or under the stomach while sleeping. It also serves to confine the sleeping person between its ends providing an anti-roll aid.

Figure 8:
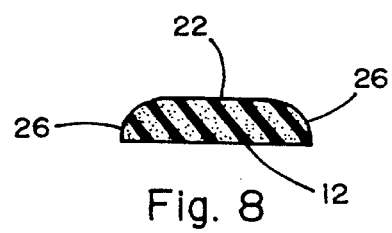
FIG. 8 is a cross-sectional view taken along the lines VIII—VIII of FIG. 2.
Figure 9:
FIG. 9 is a cross-sectional view taken along the lines IX—IX of FIG. 2.
Figure 10:
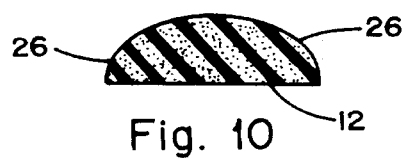
FIG. 10 is a cross-sectional view taken along the lines X—X of FIG. 2.

Pillow 10, having a generally planar bottom surface or base 12 (see FIG. 4), is formed in one piece and includes two end sections 30 joined by an elongated midsection 20, as best seen in FIG. 2. Each end section 30 comprises a pad 32 which is substantially hemispherical in shape, and has an apex or peak 34 at its top midpoint or pole, as shown in FIGS. 3, 5, and 6. Midsection 20, spanning between each oppositely spaced hemisphere 32, comprises a substantially flat lumbar support portion 22 on the top surface along and on either transverse side of midpoint 24. Base 12 is wider than the lumbar support portion 22. As best shown in FIGS. 8–10, sides 26 extend downwardly from each edge of lumbar support portion 22 in a rounded or curved fashion to the edges of base 12. Pillow 10 also has sloping surfaces 28 at the point of intersection between each hemisphere 32 and lumbar support portion 22, as shown in FIG. 5, so that there is gradual transition between midsection 20 and end sections 30, there being no exact point where one ends and the other begins. The top surfaces of the midsection between either side of the flat lumbar support portion 22 and each hemispherical end section are rounded in gentil curve across the width of the pillow from one edge of the base at bottom surface 12 to the other edge as shown in FIGS. 9 and 10.

Figure 7:
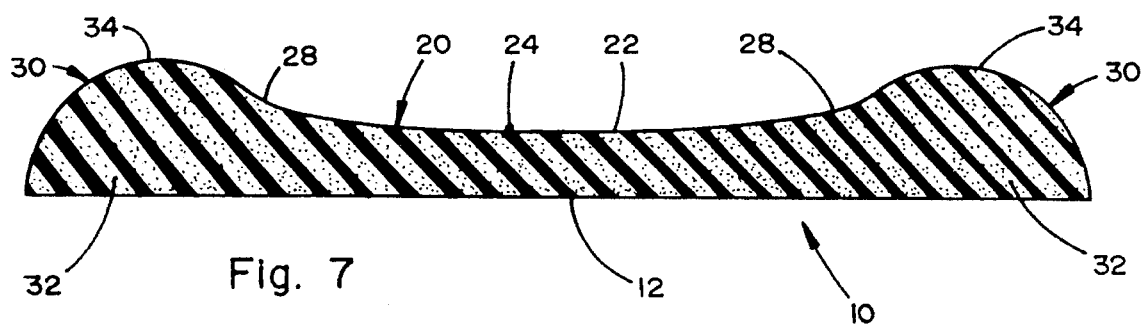
FIG. 7 is a cross-sectional view taken along the lines VII—VII of FIG. 2.
Figure 11:
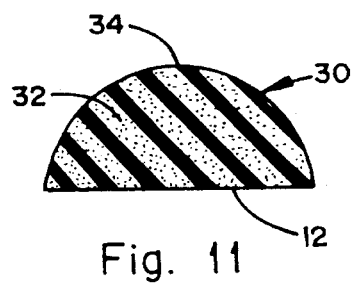
FIG. 11 is a cross-sectional view taken along the lines XI—XI of FIG. 2.

Referring now to FIG. 7, a cross-sectional view of pillow 10 taken along a line extending from each peak 34 through midpoint 24, it is seen that pillow 10 is substantially concave or saddle-like in shape. A cross section taken perpendicular to FIG. 7, that is, through the midpoint 24 but across the width of-pillow 10, shows that the shape of lumbar support portion 22 is substantially flat at this point, with rounded sides 26 extending downwardly therefrom, as shown in FIG. 8. A cross section taken across the width of pillow 10 at a point halfway between midpoint 24 and sloping surface 28 (FIG. 9), shows that lumbar support portion 22 begins to have more of an arc shape proceeding away from midpoint 24. As shown in FIG. 10, a cross section through sloping surface 28 is nearly completely rounded, although not quite semicircular. FIG. 11 shows a cross section through peak 34 of hemisphere 32, which is substantially semicircular.

Pillow 10 can be constructed of any suitable flexible, resilient material. Preferably, pillow 10 is made of a molded, resinous foam material such as polyurethane. In the preferred embodiment, pillow 10 has a density of about 2.8 lbs/ft., although other densities are also suitable.

Pillow 10 can be sized to any desired dimensions. However, in order for end sections 30 to serve as anti-roll aids and to place the appropriate pressure on the sacro-iliac joint, it is desirable for hemispheres 32 to have a radius that is greater than the height of midsection 20 at midsection 24. In the preferred embodiment, referring to FIG. 4, pillow 10 measures 28 inches long, i.e., from the end of one hemisphere bottom to the end of the opposite hemisphere bottom. Hemisphere 32 has a 3¼ inch radius and a 6½ inch diameter. Referring to FIG. 5, each hemisphere has a height of 3 inches, from base 12 to apex 34. At its midpoint 24, pillow 10 has a height or thickness of approximately 1 inch, and increases gradually moving towards sloping surface 28 and apex 34. These dimensions are merely given to illustrate the preferred embodiment and are not intended to limit the scope of the invention to these precise dimensions.

Pillow 10 can be used to relieve pressure associated with the sacro-iliac joint at the rear side of the hip bone/pelvis. To utilize pillow 10 for this function, a person must sleep on one of his or her sides. Pillow 10 is placed under that side, the person positioning himself or herself close to one of hemispheres 32, i.e., by resting the body on lumbar support portion 22 between midpoint 24 and sloping surface 28, as shown in FIG. 1. In this configuration, the weight of the person's body on pillow 10 will cause it to be wrapped around the hip area, thereby pushing hemisphere 32 into a nestled position with the sacroiliac joint. As explained below, this pressure aids in pain relief.

Figure 12:
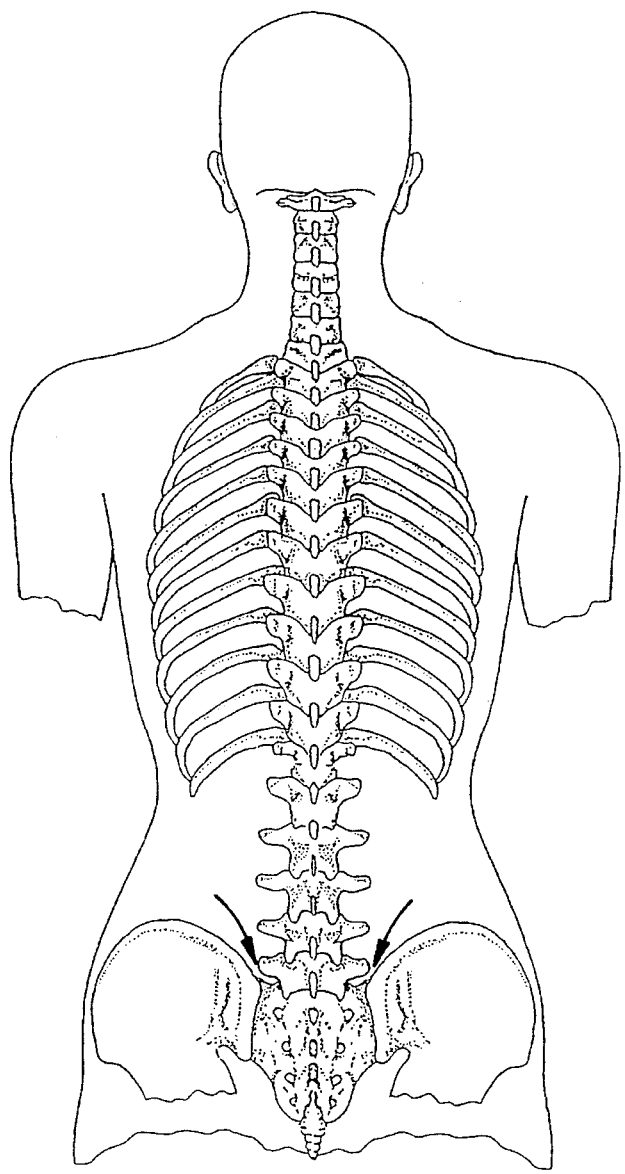
FIG. 12 is an elevation of the back of a human skeleton, showing the spine, pelvis, and sacro-iliac joint.

The sacro-iliac joint is located between the sacrum and hip bone, as shown by the arrows in FIG. 12. Therefore, pillow 10 is properly positioned when hemisphere 32 contacts the upper portion of the buttocks, slightly to one side or the other of the spine. Pillow 10 provides gentle soothing pressure when a person lays with hemisphere 32 nestled into the sacro-iliac joint. The sacro-iliac joint is a common site for back strains. Nerves can only conduct one sensation at a time. When pain occurs, it can be relieved by competing sensations. Multiple sensations, such as pain, vibration, or pressure, meet at the spinal cord at a transmission cell or T-cell. If the T-cell or gate is conducting a particular sensation, the gate will be closed to all other sensations. For example, if the T-cell or gate is conducting pressure or vibration, the T-cell will be closed to pain. This phenomenon is readily demonstrated when one bumps his or her head. The immediate reaction is usually to rub the site of injury. The gentle pressure and vibration from one's hand blunts the pain conduction. Pillow 10, with hemisphere 32 nestled against the sacro-iliac joint, takes advantage of this physiological response by placing gentle pressure at that site, thereby reducing or impeding the sensation of pain through the spinal T-cells.

The sacro-iliac joint is also a common site for referred pain from spinal nerves injured by a ruptured or bulging disk. Referred pain is pain that comes indirectly to an area of the body, such as, for example, when the left arm hurts during a heart attack. Referred pain occurs because nerves from the two different areas converge on the same location in the spinal cord. This phenomenon is called the convergence-projection hypothesis. The first sacral nerve root of the lower or lumbar spine is one of the most likely nerves to be injured from a ruptured disk because it is at the bottom of the lumbar spine. Consequently, the disk adjacent to the nerve is subjected to the greatest pressure, causing disk tears, bulges, or frank ruptures. This results in referred pain in the sacro-iliac joint, which is also soothed by pillow 10.

When a person sleeps on his or her side with pillow 10 underneath the side, pillow 10 also prevents low back pain and relieves such pain once it has occurred due to sagging or dipping of the spine. This second function is provided not only when the person is targeting the sacro-iliac joint, as described above, but also when the person positions the side of the body substantially near midpoint 24, as shown in FIG. 13, as opposed to closer to hemisphere 32 when sacro-iliac pain relief is desired. When a person sleeps on a side, the lumbar spine spans the distance between the tops of the iliac crests of the pelvis and the lower rib cage. Supported only by soft tissues, the lumbar spine conforms to the laws of gravity and can bend enough to place additional stress on the pain sensitive joints of the lumbar spine, known as the facet or apophyseal joints. If these joints are arthritic, pain will result from this stress. Pillow 10, by supplying support under the soft tissues, tends to lift and prevent this area of the spine from sagging, thereby relieving this pressure and pain. The substantially flat shape of lumbar support portion 22 across the width at midpoint 24 provides support in a comfortable fashion. Even as the lumbar support portion 22 becomes more and more arc-shaped the closer one rests to sloping surface 28 and hemisphere 32, pillow 10 is still comfortable to lie on.

A third function of pillow 10 is to relieve joint compression when one sleeps on his or her stomach, as shown in FIG. 14. Muscles are like ratchets and can move in only one direction. When sleeping on the stomach, the back muscles will slowly contract because the spine will again bend according to the laws of gravity. The spine's posture becomes more lordotic, i.e., sway-back like a horse carrying a heavy saddle. By placing pillow 10 under the stomach, the spine is supported and cannot sag or dip as much. The back muscles and lumbar facet joints will then experience less contraction, pressure, and pain.

Spinal stenosis can also be reduced by correcting exaggerated lordosis. Spinal stenosis occurs when the bony elements surrounding the nervous system of the spinal cord overgrow, as experienced with arthritis. If the cylinder of bone containing the nerves is excessively bent, the lumen is compromised. Because the pillow can help reduce lordosis, it can also help relieve pain from spinal stenosis.

Hemispheres 32 also function to restrain the person within pillow 10. It is often difficult to maintain the ideal sleeping position. However, hemispheres 32 serve as containment units because the body fits naturally within the saddle-shaped area between each peak 34. Also, if a person does manage to roll out of pillow 10, hemispheres 32 will contact other portions of the body, causing discomfort which may prompt the person using pillow 10 to wake up. The person can then properly reposition pillow 10 for a restful night's sleep.

The above description is considered that of the preferred embodiments only. Modifications of the invention will occur to those skilled in the art and to those who make or use the invention. Therefore, it is understood that the embodiments shown in the drawings and described above are merely for illustrative purposes and are not intended to limit the scope of the invention, which is defined by the following claims as interpreted according to the principles of patent law, including the Doctrine of Equivalents.

The embodiments of the invention in which an exclusive property or privilege is claimed are defined as follows:

1. A pillow for relieving lower back pain, said pillow being formed from a flexible, resilient material and comprising:
   a flexible, resilient base;
   an elongated, flexible, resilient midsection having a lumbar support portion and rounded sides extending from said support portion to said base; and
   oppositely spaced end sections integral with said midsection, said end sections being flexible, resilient and generally rounded in shape, said rounded end sections extending to a height above the thickness of said midsection;
   said pillow providing a support for portions of the body which flexes, wraps around and conforms to the body when placed under such body portions.

2. The pillow of claim 1 wherein each end section is hemispherical.

3. The pillow of claim 2 wherein said lumbar support portion of said midsection has a substantially flat top surface extending on either side of the midpoint of said midsection.

4. The pillow of claim 3 wherein said end sections each include an apex, said pillow further comprising sloping surfaces extending from said midsection to each of said apexes.

5. The pillow of claim 4 wherein said pillow has a substantially saddle-like configuration between each of said apexes.

6. The pillow of claim 5 wherein said pillow is molded in one piece.

7. The pillow of claim 6 wherein said pillow is constructed of a resilient foam material.

8. The pillow of claim 7 wherein said resilient foam material is polyurethane.

9. The pillow of claim 1 wherein said lumbar support portion of said midsection has a substantially flat top surface extending on either side of the midpoint of said midsection.

10. The pillow of claim 1 wherein said end sections each include an apex, said pillow further comprising sloping surfaces extending from said midsection to each of said apexes.

11. The pillow of claim 1 wherein said pillow has a substantially saddle-like configuration between each of said apexes.

12. The pillow of claim 1 wherein each hemispherical end section has a radius larger than the height of said midsection at the midpoint of said midsection.

13. A pillow for relieving lower back pain, said pillow being formed from a flexible, resilient material and comprising:
    a base;
    an elongated midsection having a lumbar support portion including a midpoint, a substantially flat top surface extending on either side of said midpoint, and rounded sides extending from said support portion to said base; and
    oppositely spaced end sections integral with said midsection, said end sections being hemispherical, said hemispherical end sections extending to a height above the thickness of said midsection;
    the portion of said midsection between said flat top surface of said lumbar support portion and each end section being rounded from one edge of said base to the other when viewed in transverse section.

14. A flexible, resilient pillow for relieving lower back pain, said pillow being formed in one piece from foam material and comprising:
    a flexible, resilient base having a generally planar bottom surface;
    an elongated, flexible, resilient midsection having a lumbar support portion, a midpoint, and rounded sides extending from said lumbar support portion to said base; and
    an end section at each end of and integral with said midsection, said end sections being flexible, resilient and spaced apart by said midsection with each end section being hemispherical, each hemispherical end section including a top apex, said pillow having sloping surfaces extending from said midsection to each end section;
    said pillow providing a support for portions of the body which flexes, wraps around, and conforms to the body when placed under such body portions.

15. The pillow of claim 14 wherein said lumbar support portion of said midsection has a substantially flat top surface extending on either side of the midpoint of said midsection.

16. The pillow of claim 14 wherein said pillow has a substantially saddle-like configuration between each of said apexes.

17. A flexible, resilient pillow for relieving lower back pain, said pillow being formed in one piece from foam material and comprising:
    an elongated midsection having a generally planar bottom surface, a lumbar support portion, a midpoint, and rounded sides; and
    an end section at each end of and integral with said midsection, said end sections being spaced apart by said midsection with each end section being hemispherical, each hemispherical end section including a top apex, said pillow having sloping surfaces extending from said midsection to each end section;

said lumbar support portion of said midsection having a substantially flat top surface extending on either side of said midpoint of said midsection;

the portion of said midsection between said flat top surface of said lumbar support portion and each end section being rounded from one edge of said base ro the other when viewed in transverse section.

18. A method for relieving lower back pain, comprising:

placing a pillow under a side of a person's body in the hip region and transverse to the length of the body when the person is lying on his or her side, said pillow comprising two hemispherical end sections joined by a midsection, said midsection comprising a lumbar support portion having a midpoint and rounded sides, and positioning said pillow with one of said end sections adjacent the back and the other end section adjacent the front/stomach of the person.

19. The method of claim 18 wherein said pillow is positioned between the person's iliac crests and the lower rib cage.

20. The method of claim 19 wherein the person is positioned on said midsection substantially halfway between each of said end sections, near said midpoint of said lumbar support portion.

21. The method of claim 20 wherein said pillow is positioned with one end section close to the hip, whereby the weight of the person resting on said pillow causes said pillow to wrap around the person and place said hemispherical end section in contact with the lower back, thereby placing pressure on the sacro-iliac joint.

22. The method of claim 18 including inhibiting the person from rolling out of said pillow with the end sections of said pillow.

23. The method of claim 18 wherein said pillow is positioned with one end section close to the hip, whereby the weight of the person resting on said pillow causes said pillow to wrap around the person and place said hemispherical end section in contact with the lower back, thereby placing pressure on the sacro-iliac joint.

24. A method of relieving lower back pain, comprising:

placing a pillow under a person's stomach, said pillow comprising two hemispherical end sections joined by a midsection, said midsection comprising a lumbar support portion having a midpoint and rounded sides.

25. The method of claim 24 wherein the person is positioned on said midsection substantially halfway between each of said end sections, near said midpoint of said lumbar support portion.

26. The method of claim 24 including inhibiting the person from rolling out of said pillow with said end sections.

\* \* \* \* \*

UNITED STATES PATENT AND TRADEMARK OFFICE
CERTIFICATE OF CORRECTION

PATENT NO. : 5,544,377
DATED : August 13, 1996
INVENTOR(S) : Mark L. Gostine

It is certified that error appears in the above-identified patent and that said Letters Patent is hereby corrected as shown below:

Column 6, line 4:
"fiat" should be --flat--
Column 6, line 54:
"fiat" should be --flat--
Column 7, line 8:
"fiat" should be --flat--

Signed and Sealed this

Sixth Day of July, 1999

Attest:

Q. TODD DICKINSON

*Attesting Officer*  *Acting Commissioner of Patents and Trademarks*